(12) United States Patent
Bjerneld

(10) Patent No.: US 7,811,435 B2
(45) Date of Patent: Oct. 12, 2010

(54) METHOD FOR SCANNING GELS AND GEL FOLDER FOR USE IN THE METHOD

(75) Inventor: Erik Bjerneld, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 519 days.

(21) Appl. No.: 11/719,965

(22) PCT Filed: Nov. 21, 2005

(86) PCT No.: PCT/SE2005/001745

§ 371 (c)(1),
(2), (4) Date: May 23, 2007

(87) PCT Pub. No.: WO2006/057598

PCT Pub. Date: Jun. 1, 2006

(65) Prior Publication Data

US 2008/0128280 A1 Jun. 5, 2008

(30) Foreign Application Priority Data

Nov. 25, 2004 (SE) .................................. 0402909

(51) Int. Cl.
*G01N 27/447* (2006.01)
(52) U.S. Cl. .................... 204/456; 204/461; 204/606
(58) Field of Classification Search ................ 204/450, 204/456, 600, 606, 612, 461
See application file for complete search history.

(56) References Cited

U.S. PATENT DOCUMENTS

| 4,130,824 A | * | 12/1978 | Amos et al. ............... 346/33 A |
| 4,151,065 A | | 4/1979 | Kaplan et al. |
| 4,415,428 A | | 11/1983 | Nochumson et al. |
| 4,675,300 A | * | 6/1987 | Zare et al. .................... 204/452 |
| 4,726,889 A | | 2/1988 | Love et al. |
| 5,068,019 A | * | 11/1991 | Yoshida et al. .............. 204/546 |
| 5,108,179 A | | 4/1992 | Myers |
| 5,112,736 A | | 5/1992 | Caldwell et al. |

(Continued)

FOREIGN PATENT DOCUMENTS

EP        0 753 584        1/1997

(Continued)

OTHER PUBLICATIONS

Kameoka, J., et al., "A Polymeric Microfluidic Chip for CE/MS Determination of Small Molecules", Analytical Chemistry, 2001, 73, 1935-1941.

*Primary Examiner*—Kaj K Olsen
(74) *Attorney, Agent, or Firm*—Yonggang Ji

(57) ABSTRACT

The present invention relates to a method of scanning an electrophoretic gel after electrophoresis of fluorescence labelled samples, comprising inserting the gel into a separate low fluorescent scanning unit, in the shape of a gel folder or a frame, and scanning the gel inside the gel folder or frame with a fluorescence scanner. Any gel may be scanned but if the gel is provided with a gel adherent backing the backing is first removed in a first step. The gel folder may be sealed after scanning for future analysis of the gel. The invention also relates to gel folders and frames as well as a kit with these and a hydrogel. The invention also relates to the use of these for scanning of electrophoretic gels.

6 Claims, 2 Drawing Sheets

U.S. PATENT DOCUMENTS

| | | | |
|---|---|---|---|
| 5,188,963 A * | 2/1993 | Stapleton | 435/288.3 |
| 5,458,760 A * | 10/1995 | Kozulic | 204/616 |
| 5,865,974 A * | 2/1999 | Cabilly et al. | 204/456 |
| 5,981,185 A * | 11/1999 | Matson et al. | 435/6 |
| 6,054,036 A * | 4/2000 | Izmailov et al. | 204/616 |
| 6,379,516 B1 | 4/2002 | Cabilly et al. | |
| 6,685,813 B2 * | 2/2004 | Williams et al. | 204/549 |
| 6,787,016 B2 * | 9/2004 | Tan et al. | 204/455 |
| 2002/0056639 A1 | 5/2002 | Lackritz et al. | |
| 2004/0032058 A1 * | 2/2004 | Neeper et al. | 264/328.1 |
| 2004/0050699 A1 * | 3/2004 | Goncalves | 204/450 |
| 2007/0051630 A1 * | 3/2007 | Larsson et al. | 204/616 |

FOREIGN PATENT DOCUMENTS

| | | |
|---|---|---|
| WO | WO 02/071049 | 9/2002 |
| WO | WO 03/055923 | 7/2003 |
| WO | WO2004/106911 | 12/2004 |

* cited by examiner

Step 1

Step 2

Step 3

METHOD FOR SCANNING GELS AND GEL FOLDER FOR USE IN THE METHOD

CROSS-REFERENCE TO RELATED APPLICATIONS

This application is a filing under 35 U.S.C. §371 and claims priority to international patent application number PCT/SE2005/001745 filed Nov. 21, 2005, published on Jun. 1, 2006, as WO 2006/057598, which claims priority to patent application number 0402909-6 filed in Sweden on Nov. 25, 2004; the disclosures of which are incorporated herein by reference in their entireties.

FIELD OF THE INVENTION

The present invention relates to a method for scanning electrophoretic gels used for separation of fluorescence labelled biomolecules. Furthermore, the invention relates to gel folders or frames for holding said gels during scanning and for storing said gels after scanning. According to the invention, the gel folders are made of low fluorescent material.

BACKGROUND OF THE INVENTION

Electrophoresis has been used for a long time to separate charged molecules according to their difference in migration rate under the influence of an electrical field. Traditionally, the molecules are stained in the gel after electrophoresis by more or less selective dye stains or by staining using colloidal metal particles. The molecules to be separated may also be labelled, for example with a radioactive or fluorescent label, for detection after the electrophoresis. Today it is most common to avoid the use of radioactivity in favour of fluorescent labelling, such as labelling with cyanine dyes.

However, the electrophoretic backings used to carry the electrophoretic slab gel are in many cases fluorescent per se which disturbs the detection procedure. Commonly used electrophoretic support films, such as polyethylene terephtalate (PET) function satisfactorily for relatively large amounts of fluorescence labelled biomolecules but disturb and hinder the detection of low amounts of biomolecules after slab gel electrophoresis. Since this limits the application of the technique in, for example, diagnostic assays it is very important to be able to detect very low amounts of biomolecules in for example a biological sample. Another important area is pharmacological research where most of the pharmacologically interesting proteins occur at very low concentrations compared to high abundance proteins, such as albumin.

To avoid disturbances in the detection of fluorescence labelled samples, electrophoretic supports of glass have been used. Glass enables imaging of low amounts of fluorescence labelled samples. However, glass as electrophoretic support is not desirable of space, weight and safety reasons.

Alternatively, gels are scanned without a support which, of course, minimises the fluorescence background. However, this option is not desirable because it is difficult to handle the gel before and after scanning.

It would be desirable to improve the handling of these gels.

It would also be desirable to be able to use pre-swollen ready to use gels, such as pre-cast DALT™ gels or PHAST™ gels, for fluorescence detection in such a way that scanning of low sample amounts is possible.

Furthermore, it would be desirable to scan any gel for presence of fluorescence after electrophoresis and then to store the gel in a hydrated condition for future use, such as future mass spectrometry analysis.

SUMMARY OF THE INVENTION

The present invention relates to a method of scanning electrophoretic gels run with fluorescence labelled samples.

The invention also relates to low fluorescent gel folders or frames for electrophoretic gels giving no or very little background fluorescence.

Furthermore, the invention relates to a kit comprising a low fluorescent gel folder and a hydrogel, and optionally a gel remover for detaching the gel from its backing if such a backing is present.

The present invention provides an alternative to the low fluorescent gel support described in WO 2004/106911.

In a first aspect, the invention relates to a method of scanning an electrophoretic gel after electrophoresis of fluorescence labelled samples, comprising the following steps:
a) inserting the gel into a gel folder or a frame made of low fluorescent material, and
b) scanning the gel inside the gel folder or the frame with a fluorescence scanner.

According to the invention, the gel is removed from its casting cassette and inserted into a separate scanning unit, i.e. the gel folder or frame, after electrophoresis. Preferably, the scanning unit is a gel folder.

The gel may be cast on a gel adherent backing and in that case the backing is removed before step a). The backing may be of glass or plastic and the gel adherent material may be allylglycidylagarose or silane.

The method of the invention may be used with pre-cast as well as manually cast gels and the gels may be backed with a gel adherent backing or not.

Preferably, step a) is performed in solution, i.e. under submerged conditions.

The samples are preferably proteins and the labels are preferably cyanine-derived labels. The gel may be pre-cast or cast before electrophoresis and may be any kind of hydrogel, such as agarose or polyacrylamide.

The gel folder may be any kind of folder or envelope and the frame may be a support or receptacle with one or more edges.

In order to avoid diffuse scanning patterns due to streaking of some sample proteins in the bottom most layer of backed pre-cast gels (or any gel cast with a gel adherent layer, such as allylglycidylagarose), a thin gel layer is preferably left on the backing during gel removal. For example, in the case of a 1 mm thick gel, it is suitable to leave 1-10% of the gel on the backing.

The method may comprise a further step c) in which the gel folder is sealed around its sides or edges and the gel is stored for future use, such as future analysis or for documentation purposes.

In case a frame is used, it is sealed with a top sheet or lid to keep the gel in a hydrated condition.

In a second aspect, the invention relates to a gel folder or frame for use in the above method, comprising a bottom sheet and an optional top sheet and wherein at least one of the sheets, such as the bottom sheet, is made of low fluorescent material. Preferably, the material is flexible.

If the top sheet is used on top of the gel during scanning it is preferably also made of low fluorescent material. If it is used after scanning to provide a storage lid on top of the bottom sheet with the gel there between, then the top sheet may be of any material.

If the top sheet is not present, the bottom sheet is preferably provided with edges or borders along at least three sides to form a frame which holds the gel on the bottom sheet. In an alternative embodiment, the bottom sheet is provided with two edges and the top sheet is provided with two edges so that they together may form a closed folder when sealed.

In a preferred embodiment, the bottom sheet and top sheet are sealed to form a folder or envelope, preferably they are sealed along at least one side, and more preferably along at least three sides. In this embodiment, both the bottom sheet and the top sheet are made of low fluorescent inert material.

The gel folder is preferably made of a polymer having the following formula:

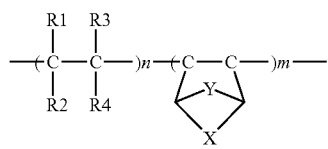

wherein n=0-100 000 m=0-100 000

R1, R2, R3 and R4=hydrogen, halogens, methyl groups or non-aromatic hydrocarbon chains (optionally containing branches or cyclic structures)

X, Y=methylene groups or non-aromatic hydrocarbon chains (optionally containing branches or cyclic structures)

Y can optionally be absent.

The gel folder of the invention is especially suitable for scanning of gels comprising samples labelled with fluorescent dyes, such as CY™-dyes, after the second dimension of 2D electrophoresis or any kind of differential gel electrophoresis (DIGE).

Preferred plastic films of the above formula are:

Polypropylene: R1=CH$_3$, R2=R3=R4=H, preferably biaxially oriented polypropylene (BOPP).

Polychlorotrifluoroethylene (PCTFE): R1=Cl, R2=R3=R4=F Polycycloolefins:

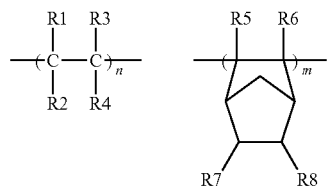

wherein n=0, R5=R6=H, or

R1=R2=R3=R4=R5=R6=H, R7, R8=H or CH$_3$

According to the invention, the plastic gel folder is made from one of the polymers above, preferably wherein R1=R2=R3=R4=R5=R6=H, R7, R8=H or CH$_3$, commercially available as ZEONOR™.

The gel folder may be used with any hydrogel, such as an acrylamide or agarose gel, cast on any kind of support, such as glass or polymer. The polymer or glass may or may not be provided with a gel adherent layer such as silane or allylglycidylagarose. According to the invention, a gel remover may if necessary be used to detach the gel from the backing and insert it into the gel folder. A special type of gel remover will be described below in connection with removal of pre-cast gels.

In a third aspect, the invention relates to a kit comprising the above gel folder and a hydrogel. The hydrogel may be any kind of hydrogel but is preferably a polyacrylamide gel, such as a DALT™ gel cast on a gel adherent polymer backing.

Furthermore, the kit may comprise a gel remover. The design of the gel remover is not critical as long as it is possible to remove a gel with it in a condition suitable for scanning. An example of a preferred gel remover is described below under the detailed description.

Preferably, the hydrogel is pre-swollen ready to use hydrogel. In this case the kit may further comprise a buffer, such as N-piperidino (or N-pyrrolidino) propionamide (PPA) buffer which keeps the gel storage stable in its swollen state. The gel may be stored in the gel folder.

In a fourth aspect, the invention relates to use of a gel folder or frame as above for scanning of electrophoretic gels. Preferably, for scanning of fluorescence labelled samples. The gel folder, or frame with a lid, may also be used to store gels before of after scanning.

The gel folder is used with enclosed hydrogel during fluorescence scanning following electrophoretic separation of fluorescence labelled biomolecules (particularly proteins, peptides and nucleotides) and is especially suitable for DIGE applications. An advantage of the gel folder of frame according to the invention is that it can be sealed after scanning to store the gel in a hydrated condition after addition of a suitable hydrating solution.

DETAILED DESCRIPTION OF THE INVENTION

Figure 1:
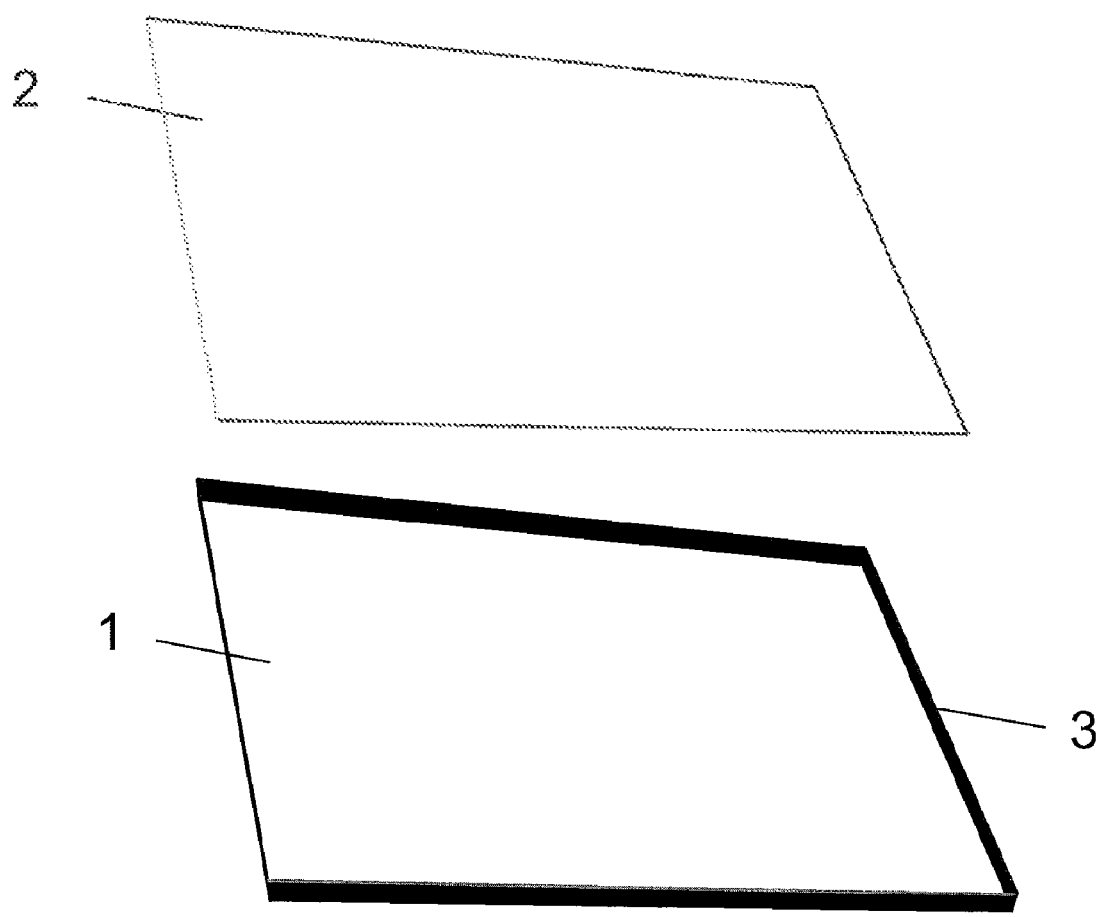
FIG. 1 is a schematic view of the gel folder according to the invention.

FIG. 1 shows an example of a low-fluorescent gel folder or frame according to the invention. The gel folder comprises a bottom sheet 1 and an optional top sheet 2.

The bottom sheet 1 may be provided with edges or borders 3, preferably along at least three sides for holding the gel onto place. In this case the bottom sheet with edges has a frame-shape. If present, the top sheet functions as a lid on top of the frame preventing the gel from drying out.

The gel folder or frame is dimensioned slightly larger than the gel to be inserted therein.

In the presently best embodiment of the invention, the bottom sheet has no edges or borders and the top sheet and bottom sheet are sealed together along three sides to form a gel folder with one opening for inserting the gel. The sealing may be done by heating, welding or by an adhesive. After insertion of the gel into the gel folder and scanning, the fourth side may be sealed for storage purposes.

In an alternative embodiment, the gel folder has a bottom and top sheet which are sealed along one side. After insertion of the gel, the three remaining sides may be sealed for storage of the gel.

An advantage of using a folder instead of a simple sheet or support is that the folder encloses the gel and it prevents the gel from drying. In addition it will keep the layer above the gel even. If no top sheet is used then an excess of water on top of the gel is required to prevent it from drying during scanning. This option is not user-friendly as the water layer tends to move and evaporate during scanning, giving rise to artefacts in the scanned image. Furthermore, if the folder is sealed then the gel can be stored in fix solution which is an effective way to store the gel for further analysis by, for example, mass spectrometry.

The gel folder should be inert and transparent and the haze value should be lower than 3%. The gel folder should have a suitable flexibility, i.e. a flexural modulus of 1300-2500 MPa.

For low fluorescence and still easy handling, the low fluorescent film is 10-200 μm thick, preferably 50-100 μm thick. A preferred example is a 75 μm ZEONOR™ film.

EXAMPLES

The present examples are provided for illustrative purposes only, and should not be interpreted in any way as limiting the scope of the invention as defined by the appended claims. All references provided below and elsewhere in the present specification are hereby included herein via reference.

Step 1: Electrophoresis on Pre-Cast Gel

A pre-cast DALT™ polyacrylamide gel was used for differential electrophoresis. The samples contained CY2™ and CY5™, minimal dye, labelled proteins. Electrophoresis was run under conventional conditions.

Step 2: Removal of Backing and Insertion of Gel into Folder

Figure 2:
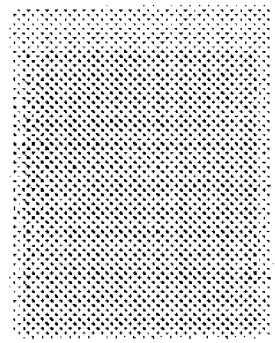
FIG. 2 schematically shows the procedure of removing a gel from its backing and inserting it into a gel folder.
Figure 2:
Figure 2:
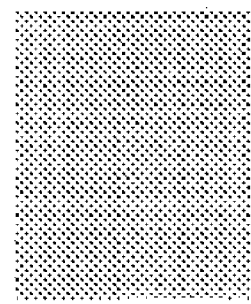
Figure 2:
Figure 2:
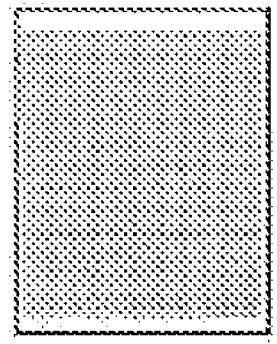

The gel adherent backing was removed with a gel remover directly after electrophoresis, i.e. prior to scanning of the gel. The gel was transferred into a low-fluorescent film folder made of 188 μm thick ZEONOR™ film. FIG. 2 shows a schematic overview of this procedure.

In one advantageous embodiment of the method according to the invention, the backing is removed while the gel is submerged in a fix solution, for example 25% EtOH and 10% HAc, to prevent the gel from expanding. The film remover (not shown) is in a preferred configuration a thin wire which is stretched between two posts. The height of the wire is adjusted to the height of the backing and then the gel is removed simply by cutting the gel using the wire. The simplicity of this tool allow for cutting in solution. After removal, the free floating gel is transferred to the gel folder in solution.

Step 3: Scanning of Gel Folders with Enclosed Gels

The low fluorescent gel folder with enclosed gel was placed on the scanner platen of a TYPHOON™ scanner. The results from the scanning showed that the folder did not cause any artefacts or give rise to an unacceptable background in scanned images of 2D-gels.

These results suggest that 2D gel maps of equal quality (as without gel folder) are attainable using a low-fluorescent folder to support the gels. Furthermore, in the experiments a 188 μm thick plastic film was used and this thickness can in this case be further reduced to decrease the fluorescence background by a factor 2-4. It is expected that a 50-100 μm thick low fluorescent film will provide the best properties with regards to fluorescence background and stability (ease of handling).

Step 4: Storing of Scanned Gels

If desirable, the gel folder is sealed to keep the gel in an aqueous environment, for example in the above fix solution, for long-term storage of the gel. In this way the gel may be used for future analysis, such as mass spectrometry analysis.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method of scanning an electrophoretic gel after electrophoresis of fluorescence labelled samples, comprising the following steps:
   a) inserting the gel into a gel folder made of low fluorescent material, said gel folder comprising a bottom sheet (1) and a top sheet (2) wherein the bottom sheet of said gel folder is provided with edges or borders (3) along at least three sides to form a frame which holds the gel on the bottom sheet, and
   b) scanning the gel inside the gel folder with a fluorescence scanner, wherein the gel is cast on a gel adherent backing and the backing is removed before step a), and wherein a thin gel layer is left on the backing.

2. The method of claim 1, further comprising:
   c) sealing the gel folder along its sides or edges and storing the gel.

3. The method of claim 1, wherein the gel folder is flexible.

4. The method of claim 1, wherein the bottom sheet and top sheet of said gel folder are sealed along at least one side.

5. The method of claim 1, wherein the bottom sheet and top sheet of said gel folder are sealed along at least three sides.

6. The method of claim 1, wherein the bottom sheet and top sheet of said gel folder are made of low fluorescent material.

\* \* \* \* \*